US010292674B2

(12) United States Patent
Kaepplinger et al.

(10) Patent No.: US 10,292,674 B2
(45) Date of Patent: May 21, 2019

(54) METHOD FOR COMPUTING A CT SCANNER PROTOCOL

(71) Applicant: Siemens Healthcare GmbH, Erlangen (DE)

(72) Inventors: Stefan Kaepplinger, Jena (DE); Robert Lapp, Nuremberg (DE); Rainer Raupach, Heroldsbach (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 268 days.

(21) Appl. No.: 15/279,972

(22) Filed: Sep. 29, 2016

(65) Prior Publication Data

US 2017/0105698 A1 Apr. 20, 2017

(30) Foreign Application Priority Data

Oct. 15, 2015 (DE) .................. 10 2015 220 107

(51) Int. Cl.
*A61B 6/00* (2006.01)
*G16H 40/40* (2018.01)
(Continued)

(52) U.S. Cl.
CPC .............. *A61B 6/582* (2013.01); *A61B 6/032* (2013.01); *A61B 6/545* (2013.01); *G06F 19/00* (2013.01);
(Continued)

(58) Field of Classification Search
CPC ......... A61B 6/582; A61B 6/032; A61B 6/545; A61B 6/542; A61B 6/563; G16H 40/40;
(Continued)

(56) References Cited

U.S. PATENT DOCUMENTS

2007/0211756 A1  9/2007 Glaser-Seidnitzer et al.
2009/0006131 A1* 1/2009 Unger ................... G06F 19/321
                                                        705/3
(Continued)

FOREIGN PATENT DOCUMENTS

CN   103358224 A   10/2013
CN   103654780 A    3/2014
(Continued)

OTHER PUBLICATIONS

Szczykutowicz T et al: "Compliance with AAPM Practice Guideline 1.A; CT Protocol Management and review—from the perspective of a university hospital"; In Journal of Applied Clinical Medical Physics; ,V. 16 N. 2; März 2015; ISSN 15259914; pp: 1-12; 2015.
(Continued)

*Primary Examiner* — Courtney D Thomas
(74) *Attorney, Agent, or Firm* — Harness, Dickey & Pierce, P.L.C.

(57) ABSTRACT

A method and a system are disclosed for image acquisition, in which the protocol for controlling the CT scanner is computed automatically. The system includes a facility, which includes at least one CT scanner; a central PACS system in which image data and assigned metadata are stored as image data information, acquired with the facility; and an analysis unit, in terms of programming technology and/or circuit technology, for analyzing the captured image data information to automatically compute therefrom, the specific operating conditions and the facility-specific protocol parameters for the CT scanner protocol.

25 Claims, 3 Drawing Sheets

(51) Int. Cl.
  *A61B 6/03* (2006.01)
  *G06F 19/00* (2018.01)
(52) U.S. Cl.
  CPC ........... *G06F 19/321* (2013.01); *G16H 40/40* (2018.01); *A61B 6/542* (2013.01); *A61B 6/563* (2013.01)
(58) Field of Classification Search
  CPC ........ G16H 50/20; G16H 10/60; G16H 50/70; G06F 19/00; G06F 19/321
  USPC ............................................... 378/4–20, 207
  See application file for complete search history.

(56) References Cited

U.S. PATENT DOCUMENTS

| | | |
|---|---|---|
| 2012/0190962 A1 | 7/2012 | Glaser et al. |
| 2013/0267842 A1 | 10/2013 | Scheuering et al. |
| 2014/0088984 A1 | 3/2014 | Oh et al. |
| 2014/0365244 A1 | 12/2014 | Lee et al. |

FOREIGN PATENT DOCUMENTS

| | | |
|---|---|---|
| CN | 104025100 A | 9/2014 |
| DE | 102006010535 A1 | 9/2007 |
| DE | 102008002882 A1 | 1/2009 |
| DE | 102011002928 A1 | 7/2012 |

OTHER PUBLICATIONS

German Office Action dated Feb. 23, 2016.
Chinese Office Action and English translation thereof dated Jul. 17, 2015.

\* cited by examiner

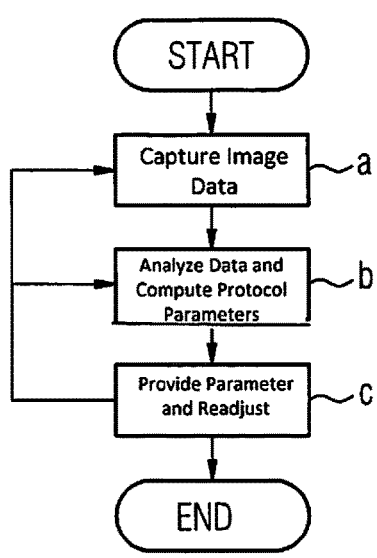
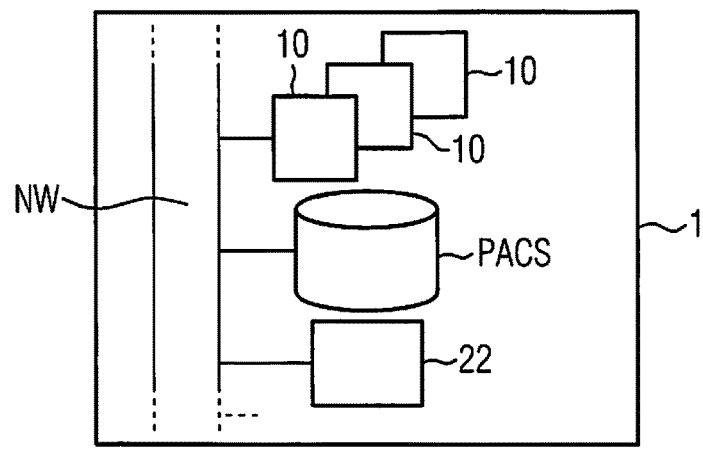
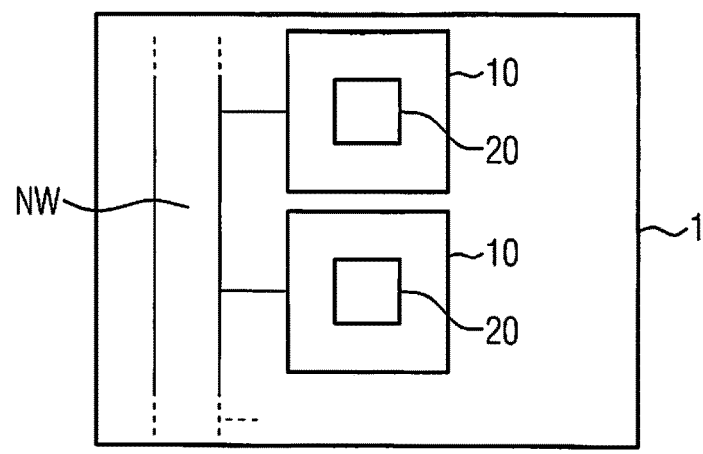

METHOD FOR COMPUTING A CT SCANNER PROTOCOL

PRIORITY STATEMENT

The present application hereby claims priority under 35 U.S.C. § 119 to German patent application number DE 102015220107.4 filed Oct. 15, 2015, the entire contents of which are hereby incorporated herein by reference.

FIELD

At least one embodiment of the present invention generally relates to a method for computing protocol parameters for a CT scanner protocol that is used for operation of a CT scanner.

BACKGROUND

During data acquisition and image reconstruction the execution of the scanner must be controlled in order to be able to capture the desired images in the required quality. To this end specific settings are grouped together in a protocol and are executed on the medical imaging device.

When a new scanner is delivered usually so-called default protocols are supplied with it, which are necessarily global or generic and are exclusively designed for the purpose of making the best possible use of the technical performance features of the scanner without taking account of the individual operating conditions of the facility for creating the images.

In practice a scanner is usually integrated into a technical facility, such as a site, an organization unit or department (e.g. a hospital department). The different medical requirements and individual preferences in the different departments, sites or organization units also make different demands on the image acquisition; the result of which is that the scanners also have to be operated and controlled under different operating conditions and with different protocols. A global preset protocol is therefore seldom able to continue to be used; it must be adapted to the operating conditions of the respective facility.

In the prior art this is usually done manually by an application specialist, who sets and adapts the relevant protocol parameters specifically for the facility during the installation of the device. In further operation further adaptations could also be undertaken directly by the customer.

The previous process has proved to be time-consuming and prone to errors, since incorrect manual settings are possible.

It is also known to import protocols from other devices or from a central entity. A corresponding "import" feature can be embodied for this purpose within the framework of scan protocol assistance software. For example DE 10 2006 010 535 describes making MR protocols available centrally for another modality (magnetic resonance). However it proves disadvantageous here in practice that the protocols with the parameters contained therein are frequently not available for various reasons (no access, no hits during a database search etc.).

If a device is replaced the protocol is not retained as a rule. Furthermore the protocols must also be readable, i.e. they must be available in readable formats. For protocols from other manufacturers this is generally not the case, since proprietary protocols are used and standardization has not yet been implemented across all manufacturers. A further complicating factor is that—even if the earlier protocol parameters are available and can be read in—the read-in (old) parameters must also be correctly interpreted, since the parameters are scanner-specific and manufacturer-specific. A 1:1 transfer (from the "old" protocol to the "new" protocol) is therefore not possible. If for example a protocol parameter defines, for a SOMATOM device of the applicant, that a specific x-ray spectrum is created for a 120 kV acceleration voltage, then because of the x-ray tubes used, the pre-filtering of the spectrum and other circumstances for other devices of other manufacturers do not necessarily match.

SUMMARY

At least one embodiment of the present invention is includes operating a CT scanner with a scanner protocol that is specifically adapted to the requirements of the respective facility and is created automatically.

Advantageous forms of embodiment are the subject matter of the claims, the description and the drawings.

A first embodiment is directed to a method for computing a CT scanner protocol for a CT scanner. The CT scanner (also just abbreviated to scanner below) may be operated in a facility under specific operating conditions.

In at least one embodiment, the method comprises the recording of image data information from images that have been acquired in the facility. The method further comprises an analysis of the captured image data information, in order automatically to deduce the operating conditions of the facility therefrom and to establish said conditions, so that on the basis of the established operating conditions, facility-specific protocol parameters for the CT scanner protocol can be computed.

According to a further embodiment, the invention relates to a protocol generator for computing a CT scanner protocol for a CT scanner, which is operated in a facility under specific operating conditions. The protocol generator can be implemented in hardware and/or in software. In at least one embodiment, it comprises:

an input interface for capturing image data information from images that have been acquired within the facility; and an analysis unit, which is intended to analyze the captured image data information by programming technology and/or circuit technology, in order automatically to compute therefrom the specific operating conditions and the facility-specific protocol parameters for the CT scanner protocol.

According to a further embodiment, the invention relates to a system for acquisition of medical images, comprising:

a facility that includes at least one CT scanner;

a central PACS system, in which image data and assigned metadata, which have been acquired within the facility, are stored; and an analysis unit which is intended to analyze the captured image data information by programming technology and/or circuit technology, in order automatically to compute therefrom the specific operating conditions and the facility-specific protocol parameters for the CT scanner protocol.

According to a further embodiment, the invention relates to a protocol generator for computing a CT scanner protocol for a CT scanner, operable in a facility under specific operating conditions, comprising:

an input interface to capture image data information from images acquired in the facility; and processing circuitry configured to execute computer-readable instructions to analyze the captured image data information to automatically compute, from the captured image data, the specific operating conditions and facility-specific protocol parameters for the CT scanner protocol.

In at least one embodiment, the processing circuitry includes at least one processor.

In at least one embodiment, the processing circuitry includes an ASIC.

According to a further embodiment, the invention relates to a non-transitory computer readable medium including program code segments which, when executed on a computer, perform at least one embodiment of the method.

The way in which embodiments are achieved has been described above on the basis of the method. Features, advantages or alternative forms of embodiment mentioned here are likewise also to be transferred to the other claimed subject matter and vice versa. In other words the physical claims (which are directed for example to a system or to a protocol generator or a scanner) can also be developed with the features that are described or claimed in conjunction with the method. The corresponding functional features of the method in such cases are embodied by corresponding physical modules, especially by hardware modules or microprocessor modules, of the system or of the facility and vice versa.

At least one further embodiment is directed to a computer program, with computer program code for carrying out all method steps of at least one embodiment of the method described in more detail above when the computer program is executed on a computer. In this case it is also possible for the computer program to be stored on a medium readable by a computer.

At least one further embodiment is directed to a computer program product, which is loaded or which can be loaded into a memory of a computer, with computer program code for performing at least one embodiment of the method described in more detail above, when the computer program is executed on the computer.

BRIEF DESCRIPTION OF THE DRAWINGS

In the more detailed description of the figures given below, example embodiments not to be understood as being restrictive, along with their features and further advantages, are discussed with reference to the drawings. In the drawings:

FIG. 2 shows a flow diagram of a method for computing protocol parameters from image data in accordance with a preferred form of embodiment of the invention;

FIG. 3 shows a further example embodiment of a system in accordance with an alternative form of embodiment of the invention;

FIG. 4 shows a further example embodiment of a system in accordance with an alternative form of embodiment of the invention.

DETAILED DESCRIPTION OF THE EXAMPLE EMBODIMENTS

Figure 1:
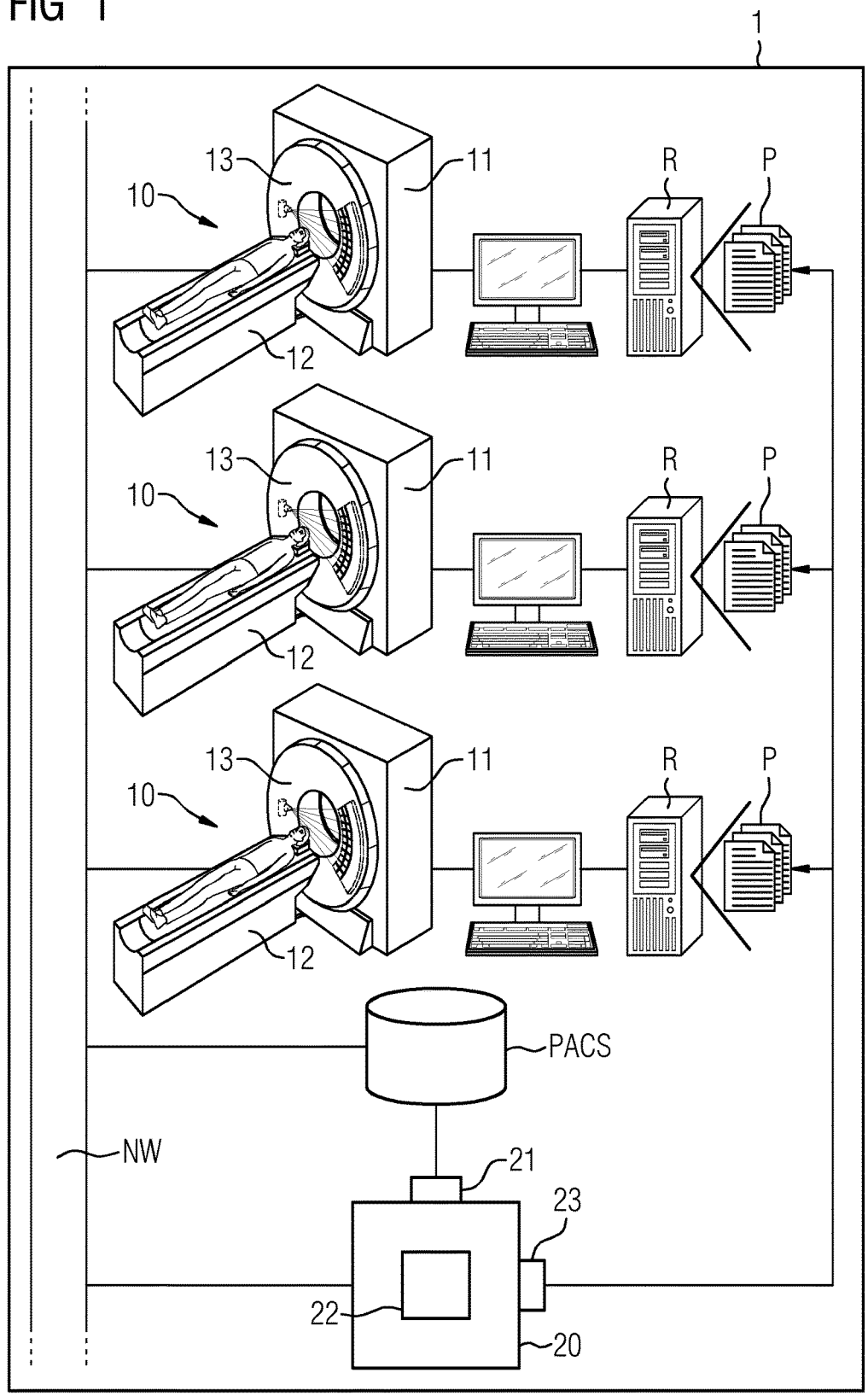
FIG. 1 shows an overview-type block diagram of a system in accordance with a preferred form of embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

In at least one embodiment, the method comprises the recording of image data information from images that have been acquired in the facility. The method further comprises an analysis of the captured image data information, in order automatically to deduce the operating conditions of the facility therefrom and to establish said conditions, so that on the basis of the established operating conditions, facility-specific protocol parameters for the CT scanner protocol can be computed.

The protocol is used to control a scanner, especially a CT scanner. It is however also to be transferred to other medical imaging devices, especially e.g. to MR devices from different manufacturers. A basic idea of at least one embodiment of the invention is based on the analysis of images (image data and/or metadata) in order to compute the protocol parameters from said images. By using the images as the basis for protocol computation, it is advantageously possible in accordance with at least one embodiment of the invention also to be able to compute the protocol parameters from third-part manufacturers and be able to provide the protocol creation in a structured, PACS-based form. The scanner is operated in a technical facility, organization unit or department (e.g. a hospital department or research unit or site). Each facility has specific requirements for the images and/or the scanner and therefore specific operating conditions, which will be taken into consideration in accordance with the invention when computing the protocol parameters.

A computation unit is used for computing the protocol parameters of the scanner protocol. The computation unit can be embodied in the form of a CPU (central processing unit) or of a co-processor or of a programmable logic module or be integrated into said units, such as e.g. into a PLD (Programmable Logic Device), an FPGA (Field Programmable Gate Array as a programmable circuit) or an ASIC (application-specific integrated circuit as an application specific integrated circuit). The computation unit comprises an analysis unit, which is designed to analyze the captured image data information, which has previously been captured in the facility, in such a way as to compute facility-specific protocol parameters therefrom without further user inputs or without further access to storage entities or computer-implemented entities.

The operating conditions characterize the operation of the scanner in the facility. The operating conditions also include specific preferences of the site or of the facility in respect of the image acquisition. A core idea of at least one embodiment of the invention is to be seen as the operating conditions being able to be extracted or read out automatically directly from the images already present and captured. To this end all images that have previously been captured with the facility (with previous/old scanners and associated protocols) are analyzed with the image data information (comprising the image data and/or the metadata), in order to compute facility-specific operating conditions therefrom.

The operating conditions include e.g. data about the selected tube voltages, the scan speed and/or the collimation as well as data about which anatomical regions are preferably to be investigated, how the slice thicknesses are specified, how the dose-to-noise ratio is defined, which reconstruction kernels are preferably to be used, which recording conditions are defined, especially head-first or feet-first settings, address(es) for forwarding the reconstructed image data, etc. The operating conditions thus characterize technical properties of the scanner and its functions (including the image reconstruction), which were employed during the acquisition of the images and can therefore also be referred to as scanner preferences.

Then, from the facility-specific operating conditions (that are calculated in accordance with the invention directly from the image data information) protocol parameters are then calculated on the basis of a protocol generation algorithm. The analysis and thus the protocol generation algorithm are executed in the analysis unit, which is preferably embodied as an integrated circuit, e.g. as an FPGA or ASIC.

In an advantageous form of embodiment of the invention, there is provision for the method to be carried out in two stages. In this embodiment of the invention the method includes an intermediate step with an intermediate result. In a first step the facility-specific operating conditions are computed from the image data information (intermediate result). In a second step the protocol parameters are calculated from the facility-specific operating conditions. This has the advantage that the intermediate result can be displayed to the user and he then has the opportunity to intervene in the process and e.g. again check or change selected conditions, so that then the subsequent computation of the protocol parameters is undertaken on the basis of the previously entered, manual changes.

In an alternative embodiment the intermediate step is omitted. The protocol parameters are computed directly from the image data information. This enables the method to be carried out fully automated and more quickly.

The image data information involves the image data per se and—optionally—meta information stored with the image data. The meta information can be stored at a separate storage location from the image data, such as e.g. centrally in a PACS (picture archiving and communication system as an image archiving system), that is responsible for or assigned to an institution, department or a site. In alternative forms of embodiment of the invention this can naturally also be a number of PACS systems or image databases, to which there is access on the part of the protocol generator. In extreme cases there can also be one image database provided for each individual scanner. As an alternative, Cloud storage of images of the respective facility can be provided, which is able to be accessed via an Internet connection (with protected access). In one form of embodiment of the invention the image data information stems from images that have been acquired on different scanners and from different manufacturers in the same facility.

The user has the opportunity to define in advance the images that are to be the basis of the protocol computation, in order to improve the quality of the computation. Sample image data that is to provide the calculation basis, which is stored in one or also in various storage locations, can be defined.

Preferably the image data is stored in accordance with the DICOM standard and has a DICOM-specific fixed format, which can be used for the purposes of the analysis. The meta information is technical data additional to the respective image data of the image study. It identifies technical acquisition parameters and includes, inter alia, recording parameters such as rotation time, collimation, number of rows, pitch, tube voltage and tube current, dose modulation type as well as reconstruction parameters such as e.g. slice thickness, reconstruction kernel, field of view, default window values etc.

In an advantageous form of embodiment of the invention there is provision for the image data information to be extracted from a DICOM file and preferably exclusively from the image header and/or from a DICOM dose SR file, wherein the files can be held in one or more central data archive(s) (PACS) or can be read in from other entities via corresponding interfaces.

According to a further advantageous form of embodiment of the invention the image data information is read in from the image header of a DICOM-formatted file. As an alternative or cumulatively, it can also be extracted from a dose file of a structured report-structured file. Advantageously the files are held in a central data archive (e.g. in a PACS).

According to a further advantageous form of embodiment of the invention the image data information comprises image noise, a spatial resolution and/or an anatomical region represented in the image.

According to a further advantageous form of embodiment of the invention the image data information is established individually in each case from an analyzed image, in order to compute image-specific protocol parameters from the image. As an alternative the image data information is averaged from a selected group of images or from all images in a pre-definable storage area, in order to compute protocol parameters covering all images but specific to the facility. This brings the advantage that the protocol parameters can be set on a broader basis of output data and are thus more valid overall. In both cases the user has the opportunity in advance of selecting or of defining the images that are to be taken as the basis for the computation. This enables the quality to be improved, in that it is e.g. excluded that artifacts are taken into account.

According to a further advantageous form of embodiment of the invention, the defined operating conditions are facility-specific and thus matching for all CT scanners of the system. This enables a unification of the scanner controls and thus also a quality improvement to be achieved.

According to a further advantageous form of embodiment of the invention, for computing the facility-specific protocol parameters, the physical performance features of the CT scanners are taken into account. The physical performance features of the scanner relate to the technical properties of the scanner, which in their turn have direct influence on the images. They include e.g. the rotation times, the tube power, the detector structure, etc. In an alternative or cumulative form of embodiment of the invention, software-based properties of the scanner are also taken into account here, such as software functionalities, the presence of licenses that enable particular functionalities etc.

According to a further embodiment, the invention relates to a protocol generator for computing a CT scanner protocol for a CT scanner, which is operated in a facility under specific operating conditions. The protocol generator can be implemented in hardware and/or in software. In at least one embodiment, it comprises:

an input interface for capturing image data information from images that have been acquired within the facility; and an analysis unit, which is intended to analyze the captured image data information by programming technology and/or circuit technology, in order automatically to compute therefrom the specific operating conditions and the facility-specific protocol parameters for the CT scanner protocol.

According to a further embodiment, the invention relates to a scanner with such a protocol generator.

According to a further embodiment, the invention relates to a system for acquisition of medical images, comprising:

a facility that includes at least one CT scanner;

a central PACS system, in which image data and assigned metadata, which have been acquired within the facility, are stored; and an analysis unit which is intended to analyze the captured image data information by programming technology and/or circuit technology, in order automatically to compute therefrom the specific operating conditions and the facility-specific protocol parameters for the CT scanner protocol.

The way in which embodiments are achieved has been described above on the basis of the method. Features, advantages or alternative forms of embodiment mentioned here are likewise also to be transferred to the other claimed subject matter and vice versa. In other words the physical claims (which are directed for example to a system or to a protocol generator or a scanner) can also be developed with the features that are described or claimed in conjunction with the method. The corresponding functional features of the method in such cases are embodied by corresponding physical modules, especially by hardware modules or microprocessor modules, of the system or of the facility and vice versa.

At least one further embodiment is directed to a computer program, with computer program code for carrying out all method steps of at least one embodiment of the method described in more detail above when the computer program is executed on a computer. In this case it is also possible for the computer program to be stored on a medium readable by a computer.

At least one further embodiment is directed to a computer program product, which is loaded or which can be loaded into a memory of a computer, with computer program code for performing at least one embodiment of the method described in more detail above, when the computer program is executed on the computer.

An embodiment of the invention is to be described in greater detail below in relation to FIG. 1. To be able to operate a CT scanner 10 in the optimum way, it is important to analyze the operating conditions of the facility 1 into which it is integrated. In accordance with the invention the operating conditions are extracted automatically from the images previously captured with the scanner 10 in the facility 1. Protocol parameters can then be computed and derived from the operating conditions.

In a facility 1 (e.g. a hospital or a department) a number of scanners 10 can be operated, which usually communicate with one another via a network NW (which can be embodied as a local network/LAN or as a WLAN). A central picture archiving system PACS is usually also located in a facility 1 and is likewise connected via the network NW to the other computer-based entities.

The scanner 10 comprises a patient table 12, a gantry 11 with one or more x-ray tube(s) 13—not shown in the figures. It is controlled via a control computer R. For the purposes of controlling the devices, a protocol P is copied onto the control computer R.

The scanner 10 is controlled via a scanner protocol P. The scanner protocol P is now to be created or adapted so that the images created with the scanner 10 will if possible be acquired in the same manner as the images previously acquired in the facility 1. To this end, when a new scanner 10 is delivered, a default scanner protocol delivered along with it can be adapted specifically to the operating conditions or an entirely new protocol can be created for the scanner 10 of the respective facility 1. To determine the protocol parameters of the protocol, in accordance with the invention, exclusively the image data information already captured in the facility 1 is analyzed. In such cases, as well as the actual image data, this optionally also involves metadata, which is assigned to the image data and for example specifies the reconstruction algorithm with which the images have been calculated, how large the image file is, which anatomical region is represented etc.

A protocol generator 20, which includes an input interface 21, via which the image data is read in from the picture archiving system PACS, is embodied to compute the scanner protocol P. Furthermore an analysis unit 22 is provided, which is intended to compute the operating conditions from the captured image data and/or metadata. The operating conditions are facility-specific. The operating conditions can however also cover all scanners; this means that all scanners 10 will be operated with matching operating conditions within a facility 1. The created protocol P is then passed on to the scanner 10 for its control. The protocol generator 20 can include an output interface 23 for this purpose.

FIG. 2 shows a typical execution sequence of the method for computing protocol parameters, which are specifically matched to the circumstances of the respective facility 1 and during this process simultaneously take account of the main performance features of the respective scanner 10. After the start of the method, in step a, the image data information is captured. This is preferably done with access to the picture archiving system PACS. In step b the image data information read in is analyzed, in order to establish, in a first intermediate result, the operating conditions of the facility 1 and then, based thereon, to compute the protocol parameters from the operating conditions. The protocol parameters computed in this way are then provided in step c. The result with the facility-specific protocol parameters can also be output at a—e.g. graphical—user interface, in order to give the user an opportunity for interaction, so that for example he can re-adjust certain of the computed parameters by hand or can request yet further images as a basis for selected parameters. This is intended to be symbolized in FIG. 2 by the arrow that branches back from step c to step a and is intended to indicate that further images are being requested as the basis for a further computation. Likewise a further analysis can be initiated. The method can also end after the provision of the protocol.

Usually the individual (old) protocols of the (old) scanner 10 are not readily available (or only with complicated measures, such as reformatting, adaptation, translation, reading in from remote entities), so that the inventive method, as described here, can be employed to derive the protocol parameters from the previous images (that have been captured with the "old" scanner that was operated with the "old" protocol). If however the "old" protocol is available in a readable format, there is provision, in a simple variant of the invention, for the settings of the "old" protocol to be translated to the new protocol to be created where possible and where the scanner performance features are available. The translation is made on the basis of a mapping specification, in which the created images represent the reference frame: The protocol of the "new" scanner 10 is to be computed so that the images created with the "new" scanner correspond as much as possible to the "old" images (created with the "old" scanner).

FIG. 3 shows an alternative structure of the inventive system according to an alternative form of embodiment of the invention. The facility 1 includes a number of CT scanners 10, a central picture archive PACS for the facility 1, i.e. facility-specific, but for all scanners. Thus the images held in the picture archive PACS, which are employed for analysis, are likewise facility-specific but for all scanners. The facility 1 is however only assigned one analysis unit 22, which can directly read in and process data over the network from the picture archive PACS, in order to derive the operating conditions from the images on which the previous acquisition of the analyzed images has been based. The analysis unit 22 can be realized as an integrated circuit in hardware or as a program in software. The output of the analysis unit 22 is then computed protocol parameters for the scanner protocol P, which can subsequently be forwarded to all or to selected scanners 10 for control thereof. This has the advantage that the user can again select at this point the scanner 10 of the facility 1 on which he would actually like to have the computed protocol executed.

FIG. 4 shows a further alternative structure of the inventive system according to a further form of embodiment of the invention. As in FIG. 3, once again a number of scanners 10 are integrated into a facility 1. In this case however each scanner 10 is expanded by an additional module. The additional module is the protocol generator 20, which can be implemented directly on the scanner 10 or on the control or computation unit assigned to it. The protocol generator 20 can be realized as an integrated circuit in hardware or as a program in software. In this form of embodiment the output of the protocol generator 20 is the computed protocol parameters for the scanner protocol P, which subsequently—just as described above in the form of embodiment of the invention that has been described in relation to FIG. 3 and with the advantages mentioned there—can be forwarded to all or to selected scanners.

Figure 5:
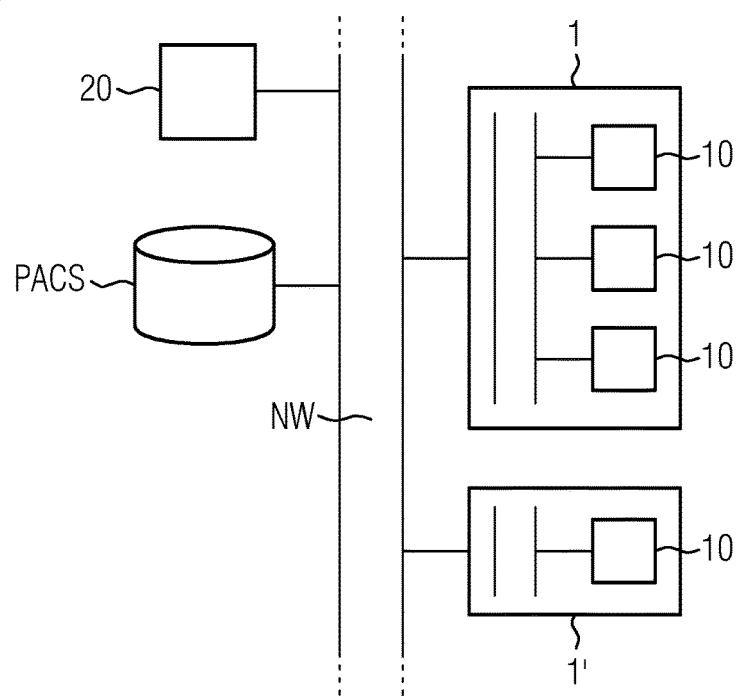
FIG. 5 shows a further example embodiment of a system in accordance with an alternative form of embodiment of the invention.

FIG. 5 shows a further advantageous alternative structure of the inventive system according to a further form of embodiment of the invention. As in FIG. 3, once again a number of scanners 10 are integrated or grouped together into a facility 1. They can communicate via an internal network and are in communication with the picture archive PACS, which can act as a database and in respect of function is assigned to the respective facility 1, via the network NW for exchange of data, and exchange data with the protocol generator 20, which is likewise assigned to the respective facility 1. This embodiment proves to be advantageous if an expansion of the inventive protocol generation to further scanners 10 beyond the respective facility 1 is desired. Thus for example it can be that similar or the same operating conditions also obtain on other scanners 10 of other facilities 1' (e.g. because the same anatomical regions are being examined in another department or in another institution). In this case it is desirable also to distribute the created protocol P to these scanners 10, although they are "actually" located outside the facility 1.

The analysis unit 22 is basically designed so that, in addition to the image data—and depending on the form of embodiment of the invention, assigned metadata—also including the performance characteristic of the scanner 10, is employed as an input variable in order to compute and to optimize the protocol parameters therefrom. The basis of the computation is always the result, i.e. the image generated with the scanner protocol, which where possible is to be similar to the already available (old or original) image that has already been created on the scanner. In this case optimization criteria (e.g. by prioritization of the input variables) can be taken into account. According to the invention it thus has an influence on the computation of the protocol parameters whether the scanner 10 will be operated e.g. with rotation times of 0.28, 0.5 or 1.9 seconds, which detector will be used and how large its detection surface is (e.g. 64×0.6 mm), whether 1 or 2 x-ray tubes (dual scan mode) are installed, how quickly the table moves, which image reconstruction algorithms are applied and/or how the control of the scan process will be performed (e.g. with a dose modulation over different anatomical regions, in order to be able to make the optimum possible signal quality available).

A protocol P can consist of a sequence of images or scans and of reconstructions assigned to the respective scans. As a result of the different reconstruction algorithms to be applied, this can once again have an influence on the image acquisition, e.g. in order to establish a slightly modified image segment or another orientation of the scans.

In an advantageous form of embodiment of the invention the stored image data and image data information is used in order to compute the operating conditions or the protocol parameters directly therefrom. In an alternative embodiment it is possible to carry out the computation of the protocol parameters on the basis of averaged values of different images, in order to make the computation result safer.

In a preferred form of embodiment of the invention the image data, the metadata (assigned to the image data) and the performance features of the scanner are taken into account as input variables for the protocol computation.

According to one embodiment of the invention some of the properties computed directly from the image data by an image analysis are as follows:

Image noise;

Spatial resolution;

Positioning and size of the anatomical region represented and reconstructed in the image;

Slice thickness; and/or

Reconstruction increment.

According to at least one embodiment of the invention, some of the properties that can be computed from the meta information, especially from the DICOM header or the Dose SR file, are as follows:

Number of reconstruction kernels for the image reconstruction; and/or

Applied dose.

Under some circumstances the properties that were mentioned above for the image data and the computations relating thereto can also be computed from the meta information, such as slice thickness, spatial resolution etc.

In other words, in accordance with at least one embodiment of the invention, one or more cost functions is or are defined depending on technical parameters of the scanner (e.g. kV, mAs, slice thickness, reconstruction algorithm, . . . ), which measure(s) the comparability of diagnostically or technically (e.g. precision, dose) relevant variables. Subsequently the parameter combination that minimizes the cost function(s) is selected as the optimum. It is also possible for each technical variable to be compared and optimized individually and practically separately.

EXAMPLES

Tube voltage: In the simplest case K(kV)=abs(kV_ref−kV) is to be minimized; somewhat more complex: K(kV, prefilter))=abs(focal point(spectrum(kV_ref, prefilter_ref)−focal point(spectrum(kV, filter))) are to be minimized, which represents a simultaneous optimization for two technical parameters.

Reconstruction algorithm: K(Kern)=abs(rho50(MTF(Kern_ref))−rho50(MTF(Kern))) is to become minimal.

A series of advantages can be achieved with at least one embodiment of the invention. Thus error-prone user interaction for computing and setting the protocol parameters is no longer necessary. Furthermore—by contrast with the procedure according to the prior art—no images of the patient have to be recorded any longer. The protocol parameters are computed solely and directly on the basis of images already acquired. Thus the radiation load on the patient can be reduced. The fact that the method is able to be carried out fully automatically enables the protocol to be created in a significantly shorter time, which leads to a better device utilization.

Finally it should be pointed out that the description of embodiments of the invention and the example embodiments are basically not to be understood as restrictive in respect of a specific physical realization of embodiments of the invention. All features explained and shown in connection with individual forms of embodiment of the invention can be provided in a different combination in the inventive subject matter in order to realize its advantageous effects at the same time.

For a person skilled in the art it is especially obvious that embodiments of the invention can be applied not just to CT devices, but also to other x-ray-based modalities, for which conclusions about the operating conditions can be drawn from the captured images, which then in their turn have an influence on the protocol parameters for device control. Furthermore the components of the protocol generator 20 can be realized distributed over a number of physical products.

The area of protection of embodiments of the present invention is given by the claims below and is not restricted by the features explained in the description or shown in the figures.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for computing a CT scanner protocol for a CT scanner, operable in a facility under operating conditions specific to the facility, the method comprising:

capturing image data information from images acquired in the facility; and computing, from the image data information captured, the operating conditions specific to the facility; and computing, from the image data information captured and the operating conditions computed, facility-specific protocol parameters for the CT scanner protocol, wherein the computing of the operating conditions and the computing of the facility-specific protocol parameters are implemented, by processing circuitry of the CT scanner, to compute the CT scanner protocol of the CT scanner.

2. The method of claim 1, wherein scanner preferences are established from the image data information captured as an intermediate result, and wherein the facility-specific protocol parameters are computed from the scanner preferences established.

3. The method of claim 2, wherein the image data information is captured from at least one of a DICOM image header file and a DICOM dose SR file of images acquired in the facility, and wherein the at least one of a DICOM image header file and a DICOM dose SR file are stored in a central data archive of the facility.

4. The method of claim 2, wherein the image data information comprises at least one of image noise, a spatial resolution and an anatomical region represented in the images acquired in the facility.

5. The method of claim 2, wherein at least one of
the image data information is established from one of the images acquired in the facility, in the computing of the facility-specific protocol parameters; and
the image data information is averaged from a selected group of the images acquired in the facility or from all of the images acquired in the facility, in the computing of the facility-specific protocol parameters.

6. The method of claim 1, wherein the image data information is captured from at least one of a DICOM image header file and a DICOM dose SR file of images acquired in the facility, and wherein the at least one of a DICOM image header file and a DICOM dose SR file are stored in a central data archive of the facility.

7. The method of claim 6, wherein the image data information comprises at least one of image noise, a spatial resolution and an anatomical region represented in the images acquired in the facility.

8. The method of claim 6, wherein at least one of
the image data information is established from one of the images acquired in the facility, in the computing of the facility-specific protocol parameters; and
the image data information is averaged from a selected group of the images acquired in the facility or from all of the images acquired in the facility, in the computing of the facility-specific protocol parameters.

9. The method of claim 1, wherein the image data information comprises at least one of image noise, a spatial resolution and an anatomical region represented in the images acquired in the facility.

10. The method of claim 9, wherein at least one of
the image data information is established from one of the images acquired in the facility, in the computing of the facility-specific protocol parameters; and
the image data information is averaged from a selected group of the images acquired in the facility or from all of the images acquired in the facility, in the computing of the facility-specific protocol parameters.

11. The method of claim 1, wherein at least one of
the image data information is established from one of the images acquired in the facility, in the computing of the facility-specific protocol parameters; and
the image data information is averaged from a selected group of the images acquired in the facility or from all of the images acquired in the facility, in the computing of the facility-specific protocol parameters.

12. The method of claim 1, wherein the operating conditions are facility-specific to the facility and are usable for all of a plurality of CT scanners of the facility, including the CT scanner.

13. The method of claim 1, wherein physical or technical performance features of the CT scanner are used in the computing of the facility-specific protocol parameters.

14. A non-transitory computer readable medium including program code segments which, when executed on a computer, perform the method of claim 1.

15. A protocol generator for computing a CT scanner protocol for a CT scanner, operable in a facility under operating conditions specific to the facility, comprising:
an input interface to capture image data information from images acquired in the facility; and
at least one processor to execute computer-readable instructions to compute, from the image data information captured, the operating conditions specific to the facility and to compute, from the image data information captured and the operating conditions computed, facility-specific protocol parameters for the CT scanner protocol, wherein the at least one processor is a component of the CT scanner and is configured to compute the CT scanner protocol of the CT scanner.

16. A CT scanner comprising the protocol generator of claim 15.

17. The protocol generator of claim 15, wherein at least one of
the image data information is established from one of the images acquired in the facility, in the computing of the facility-specific protocol parameters; and
the image data information is averaged from a selected group of the images acquired in the facility or from all of the images acquired in the facility, in the computing of the facility-specific protocol parameters.

18. A system for image acquisition, comprising:
a facility, including at least one CT scanner;
a central archive, to store image data and metadata assigned to the image data, acquired within the facility; and
processing circuitry, for each of the at least one CT scanner, to configured to execute computer-readable instructions to compute, from the image data and metadata assigned to the image data, operating conditions specific to the facility and to compute, from the image data and metadata assigned to the image data and from the operating conditions computed, facility-specific protocol parameters for a protocol of the at least one CT scanner, wherein the processing circuitry is a component of the at least one CT scanner and is configured to compute the protocol of the at least one CT scanner.

19. The system of claim 18, wherein the processing circuitry includes an application-specific integrated circuit (ASIC).

20. The system of claim 18, wherein the processing circuitry includes a field programmable gate array (FGPA).

21. The system of claim 18, wherein at least one of
the image data and metadata assigned to the image data is established from one of the images acquired in the facility, in the computing of the facility-specific protocol parameters; and
the image data and metadata assigned to the image data is averaged from a selected group of the images acquired in the facility or from all of the images acquired in the facility, in the computing of the facility-specific protocol parameters.

22. A protocol generator for computing a CT scanner protocol for a CT scanner, operable in a facility under operating conditions specific to the facility, comprising:
an input interface to capture image data information from images acquired in the facility; and
processing circuitry configured to execute computer-readable instructions to compute, from the image data information captured, the operating conditions specific to the facility and to compute, from the image data information captured and the operating conditions computed, facility-specific protocol parameters for the CT scanner protocol, wherein the processing circuitry is a component of the CT scanner and is configured to compute the CT scanner protocol of the CT scanner.

23. The protocol generator of claim 22, wherein the processing circuitry includes an application-specific integrated circuit (ASIC).

24. The protocol generator of claim 22, wherein the processing circuitry includes a field programmable gate array (FGPA).

25. The protocol generator of claim 22, wherein at least one of
the image data information is established from one of the images acquired in the facility, in the computing of the facility-specific protocol parameters; and
the image data information is averaged from a selected group of the images acquired in the facility or from all of the images acquired in the facility, in the computing of the facility-specific protocol parameters.

\* \* \* \* \*